(12) United States Patent
Lin (10) Patent No.: US 7,708,691 B2
(45) Date of Patent: May 4, 2010

(54) APPARATUS AND METHOD FOR REAL TIME 3D BODY OBJECT SCANNING WITHOUT TOUCHING OR APPLYING PRESSURE TO THE BODY OBJECT

(75) Inventor: Shengtz Lin, Cupertino, CA (US)

(73) Assignee: SonoWise, Inc., San Jose, CA (US)

( * ) Notice: Subject to any disclaimer, the term of this patent is extended or adjusted under 35 U.S.C. 154(b) by 432 days.

(21) Appl. No.: 11/193,935

(22) Filed: Jul. 29, 2005

(65) Prior Publication Data

US 2006/0241430 A1   Oct. 26, 2006

Related U.S. Application Data

(60) Provisional application No. 60/658,889, filed on Mar. 3, 2005.

(51) Int. Cl.
A61B 8/00 (2006.01)
(52) U.S. Cl. .................. 600/437; 600/439; 600/443; 600/447; 600/459; 600/462
(58) Field of Classification Search ............... 600/407, 600/437, 439, 443
See application file for complete search history.

(56) References Cited

U.S. PATENT DOCUMENTS

| | | | |
|---|---|---|---|
| 4,338,948 A * | 7/1982 | Perez-Mendez et al. ..... 600/437 |
| 4,455,872 A | 6/1984 | Kossoff et al. |
| 5,052,394 A | 10/1991 | Carpenter et al. |
| 5,181,778 A * | 1/1993 | Beller ........................ 374/119 |
| 5,335,209 A * | 8/1994 | Jaenke et al. ................ 367/155 |
| 5,339,282 A | 8/1994 | Kuhn et al. |
| 5,435,312 A * | 7/1995 | Spivey et al. ............... 600/448 |
| 5,437,281 A | 8/1995 | Lin et al. |
| 5,549,638 A * | 8/1996 | Burdette ....................... 601/3 |
| 5,551,432 A | 9/1996 | Iezzi |
| 5,664,573 A | 9/1997 | Shmulewitz |
| 5,713,356 A * | 2/1998 | Kruger ....................... 600/407 |
| 6,023,632 A * | 2/2000 | Wilk ......................... 600/407 |

(Continued)

OTHER PUBLICATIONS

Speed of sound, [online] [retrieved on Sep. 23, 2005]. Retrieved from the Internet <URL: http://www.amershamhealth. com/medcyclopaedia/medical/Volume%201/Speed%200F%20SOUND>.

*Primary Examiner*—Brian Casler
*Assistant Examiner*—Baisakhi Roy
(74) *Attorney, Agent, or Firm*—K&L Gates LLP (57) ABSTRACT

An ultrasonic image scanning system for scanning an organic object includes a container for containing a coupling medium for transmitting an ultrasonic signal to the organic object disposed therein whereby a simultaneous multiple direction scanning process may be carried out without physically contacting the organic object. The ultrasonic image scanning system further includes ultrasound transducers for transmitting the ultrasonic signal to the organic object through the coupling medium without asserting an image deforming pressure to the organic object. These transducers distributed substantially around a two-dimensional perimeter of the container and substantially at symmetrical angular positions at approximately equal divisions of 360 degrees over a two-dimensional perimeter of the container. The transducers are further movable over a vertical direction alone sidewalls of the container for a real time three dimensional (3D) image data acquisition. The container further includes sidewalls covered with a baffle layer for reducing an acoustic reverberation.

28 Claims, 6 Drawing Sheets

U.S. PATENT DOCUMENTS

| | | |
|---|---|---|
| 6,080,108 A | 6/2000 | Dunham |
| 6,108,439 A | 8/2000 | Ishiguro |
| 6,117,080 A | 9/2000 | Schwartz |
| 6,190,915 B1 * | 2/2001 | Madsen et al. .................. 436/8 |
| 6,248,071 B1 | 6/2001 | Lin |
| 6,285,904 B1 | 9/2001 | Weber et al. |
| 6,287,259 B1 | 9/2001 | Grunwald |
| 6,322,511 B1 | 11/2001 | Guracar et al. |
| 6,338,716 B1 | 1/2002 | Hossack et al. |
| 6,540,681 B1 | 4/2003 | Cheng et al. |
| 6,547,730 B1 | 4/2003 | Lin et al. |
| 6,701,341 B1 | 3/2004 | Wu et al. |
| 6,780,153 B2 | 8/2004 | Angelsen et al. |
| 6,783,497 B2 | 8/2004 | Grenon et al. |
| 6,824,514 B2 | 11/2004 | Poland et al. |
| 6,839,762 B1 | 1/2005 | Yu et al. |
| 6,926,672 B2 * | 8/2005 | Moore et al. ................. 600/459 |
| 6,969,352 B2 | 11/2005 | Chiang et al. |
| 7,266,407 B2 * | 9/2007 | Li et al. ...................... 600/430 |
| 2001/0027278 A1 | 10/2001 | Kaufman et al. |
| 2003/0125625 A1 | 7/2003 | Kelly et al. |
| 2003/0199765 A1 * | 10/2003 | Stetten et al. ............... 600/439 |
| 2004/0006272 A1 | 1/2004 | Vortman et al. |
| 2004/0059221 A1 | 3/2004 | Azuma et al. |
| 2005/0148899 A1 * | 7/2005 | Walker et al. ............... 600/553 |
| 2005/0251042 A1 * | 11/2005 | Sandrin et al. ............... 600/443 |
| 2005/0256406 A1 | 11/2005 | Barthe et al. |
| 2006/0094959 A1 | 5/2006 | Lin et al. |
| 2006/0094960 A1 | 5/2006 | Phung |
| 2006/0111634 A1 | 5/2006 | Wu |
| 2007/0083110 A1 | 4/2007 | Lin et al. |
| 2007/0276246 A1 | 11/2007 | Lin |
| 2008/0119735 A1 | 5/2008 | Lin et al. |

* cited by examiner

Example Probe Input to HV Mux output connection for an embodiment

| | | Group 1 | Group 2 | OUT Group 15 | Group 15 | Group 16 |
|---|---|---|---|---|---|---|
| IC1 | | 1<br>2<br>3<br>4<br>5<br>6<br>7<br>8 | 1<br>2<br>3<br>4<br>5<br>6<br>7<br>8 | 1<br>2<br>3<br>4<br>5<br>6<br>7<br>8 | 1<br>2<br>3<br>4<br>5<br>6<br>7<br>8 | 1<br>2<br>3<br>4<br>5<br>6<br>7<br>8 |
| IC2 | | 9<br>10<br>11<br>12<br>13<br>14<br>15<br>16 | 9<br>10<br>11<br>12<br>13<br>14<br>15<br>16 | 9<br>10<br>11<br>12<br>13<br>14<br>15<br>16 | 9<br>10<br>11<br>12<br>13<br>14<br>15<br>16 | 9<br>10<br>11<br>12<br>13<br>14<br>15<br>16 |
| IC8 | | 57<br>58<br>59<br>60<br>61<br>62<br>63<br>64 | 57<br>58<br>59<br>60<br>61<br>62<br>63<br>64 | 57<br>58<br>59<br>60<br>61<br>62<br>63<br>64 | 57<br>58<br>59<br>60<br>61<br>62<br>63<br>64 | 57<br>58<br>59<br>60<br>61<br>62<br>63<br>64 |
| IC9 | | 65<br>66<br>67<br>68<br>69<br>70<br>71<br>72 | 65<br>66<br>67<br>68<br>69<br>70<br>71<br>72 | 1<br>2<br>3<br>4<br>5<br>6<br>7<br>8 | 65<br>66<br>67<br>68<br>69<br>70<br>71<br>72 | 65<br>66<br>67<br>68<br>69<br>70<br>71<br>72 |
| IC15 | | 113<br>114<br>115<br>116<br>117<br>118<br>119<br>120 | 113<br>114<br>115<br>116<br>117<br>118<br>119<br>120 | 49<br>50<br>51<br>52<br>53<br>54<br>55<br>56 | 113<br>114<br>115<br>116<br>117<br>118<br>119<br>120 | 113<br>114<br>115<br>116<br>117<br>118<br>119<br>120 |
| IC16 | | 121<br>122<br>123<br>124<br>125<br>126<br>127<br>128 | 121<br>122<br>123<br>124<br>125<br>126<br>127<br>128 | 57<br>58<br>59<br>60<br>61<br>62<br>63<br>64 | 121<br>122<br>123<br>124<br>125<br>126<br>127<br>128 | 121<br>122<br>123<br>124<br>125<br>126<br>127<br>128 |

FIG. 11

APPARATUS AND METHOD FOR REAL TIME 3D BODY OBJECT SCANNING WITHOUT TOUCHING OR APPLYING PRESSURE TO THE BODY OBJECT

This application is a Formal application and claims a Priority Filing Date of Mar. 3, 2005 benefited from a previously filed Application 60/658,889 filed previously by the inventor of this patent application.

FIELD OF THE INVENTION

This invention generally relates to system and method for carrying out a medical imaging process. More particularly, this invention relates to an ultrasonic imaging apparatus and method for tissue scanning to improve the accuracy and early detection of breast cancer through the image scanning and analyses processes.

BACKGROUND OF THE INVENTION

Even though an early detection of cancer tissues through image scanning is very desirable to greatly improve the curing rates and also the general technologies for image scanning have made significant advancements, there are still technical difficulties and limitations faced by application of ultrasonic imaging for real time three dimensional (3D) breast scanning. Specifically, the accuracy of measurements is still not reliable due to several factors as will be further discussed below.

The mammogram scan is a preferred technique for screening of breast cancer according to the United State governmental health policy. This is mainly because of a relatively low cost and high efficiency to perform the mammogram scans. However, the accuracy of mammogram results is still questionable for women with dense breasts. Conventionally, ultrasound imaging can be used for the breast cancer screening application. U.S. Pat. No. 6,117,080, "Ultrasonic imaging apparatus and method for breast cancer diagnosis with the use of volume rendering", (the '080 patent) describes one conventional system and method for ultrasound imaging for breast cancer screening. However, conventional ultrasound imaging is merely suitable as a complementary solution for breast cancer screening. This limitation is due to the fact that the result of ultrasound imaging is strongly dependent on the skill of the person conducting the scanning. Therefore, the data and the diagnostic results are not consistently reliable.

Figure 1A:
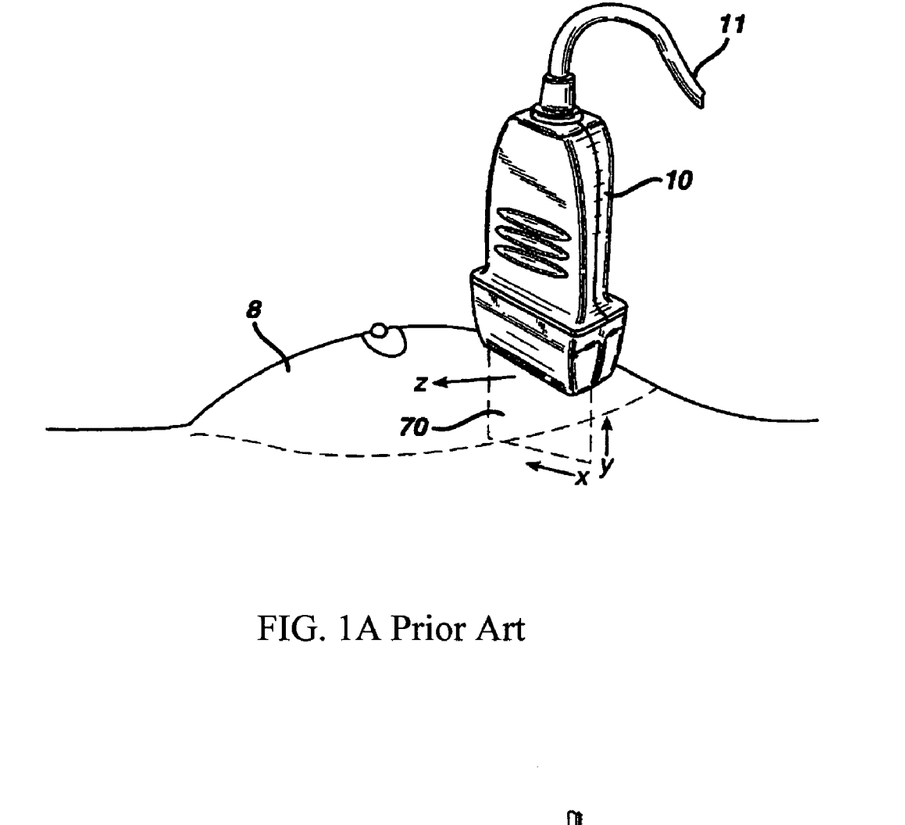
FIGS. 1A and 1B are perspective views for illustration a prior art scanning system disclosed in a prior art patent.

In a conventional ultrasound imaging for breast cancer screening, as described in the '080 patent, the breast is scanned by sliding the scanhead over the surface of the breast. The scanhead needs to be held in a constant vertical orientation so that the images are acquired from substantially parallel scan planes. Due to the variation in breast tissue thickness across the breast, the scanhead will generally move in a slight arc in the y direction as that shown in FIG. 1A according to the '080 patent's coordinate system, as the scanhead moves across the breast surface. Further, when the clinician is performing the scanning, the process maintains a constant acoustic contact with the breast and that asserts a certain amount of pressure as the scanhead moves. The constant pressure thus slightly compresses the breast tissue beneath the scanhead that leads to degradation of the accuracy and quality of data obtained from the ultrasonic image scans. The '080 patent suggested a scanning of the breast by freehand in which the user has to move the scanhead at a constant rate so that the image planes are separated in the z dimension by a substantially uniform separation which requires a few trials with slow scanhead movement and more rapid scanhead movement so the user can arrive at a scanning speed which will produce the best images. This level of skill requires significant training and practice thus limit the usefulness and acceptance of data obtained from the full breast scanning due to concerns of variations of the scanning process that may heavily depend on the skill level of an image scan operator.

The '080 patent further suggested that the arc in the y direction mentioned above can be minimized with the breast flattened out somewhat when the patient is reclining and with a water bag in between the scanhead and the breast tissue which conforms to the contours of the breast and provides good acoustic coupling between a scanning surface and the breast. This method is time consuming and does not give a consistent result and is limiting in other ways. For example, the water bag is suitable only for scanning in a down direction. Therefore, any scanning that is desired in other directions for tomography would need to take place without the water bag. However, because the water bag compresses the breast, the scans that are performed with and without the water bag would not match well.

Figure 1B:
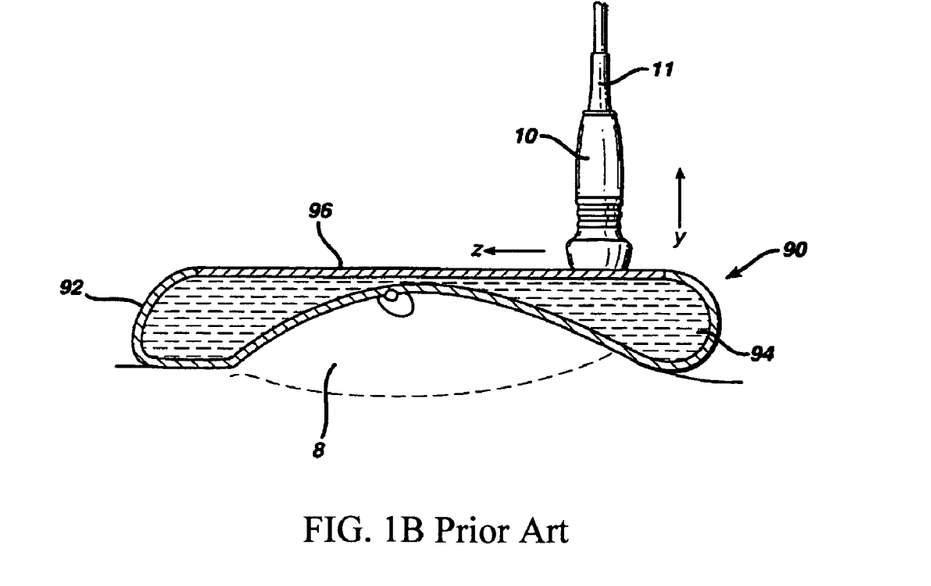

As shown in FIG. 1B, the '080 patent also suggested an external devices attached to the scanhead to assist in determining scanhead position during a scan. A linear movement-sensing device is mounted on the scanning surface of the scanning aid and the linear sensor in the housing provides signals indicative of the position of the scanhead by means of a cable, which connects to the ultrasound system through a connector. This method again does not addressing the problem of unreliable data obtained in a scan process that requires the scan head to have multi-dimensional movement during the scan.

For these reasons, a need still exists for those of ordinary skill in the art to provide an improved method and system for medical imaging. Specifically, it is desirable that the scanning system and methods are carried out without asserting pressure onto the scanning object such that more accurate scan measurements can be obtained. It is further desirable that the scan process is automated and standardized for 3D volume data acquisition such that human operations and potential errors and variations can be minimized.

SUMMARY OF THE INVENTION

It is an object of the present invention to provide a body object scanning system by applying an ultrasonic scanning device transmitting an ultrasonic waves through a coupling medium and to receive a reflection from the body object for processing and constructing a complete three dimensional image of the body object. The accuracy of the scanning and image construction are improved because there are no direct physical contact with the body object and there is no pressure asserted to the scanning object.

In another aspect, the present invention provides an ultrasonic image scanning with automatic scanning process not depending on human skill whereby standardized processes may be implemented to obtain reliable and consistent image scanning data to more accurately process and determine whether there are physical abnormalities of the scanning body object.

In yet another aspect, the present invention further provides an ultrasonic imaging scanning system that includes array of ultrasonic sensors whereby physical movement of the sensing system is not required in the 360 degree viewing of the 2D image to further simplify the scanning processes and to improve the accuracy of the scanning results.

In yet another aspect, the present invention provides a method of demultiplexing and multiplexing the ultrasonic image scanning processes from different viewing angle by alternately turning on the scanning sensors according to a time demultiplexed sequence and multiplexing the signals measured from the array of sensors for transmitting and processing the multiplexed signals to construct a three dimensional scan image of a body object. Improvement of accuracy is achieved by implementing signal processing algorithms in managing and processing these images from 360 degrees of viewing angles in X-Y dimension and different positions in Z axis.

These and other objects and advantages of the present invention will no doubt become obvious to those of ordinary skill in the art after having read the following detailed description of the preferred embodiment, which is illustrated in the various drawing figures.

BRIEF DESCRIPTION OF FIGURES

The present invention is described in detail below with reference to the following Figures.

DESCRIPTION OF PREFERRED EMBODIMENTS

Among some embodiments of the present invention are a system and a method capable of performing full breast ultrasound scanning in a relatively inexpensive way. Among some embodiments of the present invention are a 3-dimensional Computer Aided Diagnostic (CAD) software package that detects breast cancer on a screening basis.

Medical imaging systems are known. For example, ultrasound imaging is discussed in the '080 patent and in U.S. Pat. No. 6,248,071, which are hereby incorporated by reference in its entirety for all purposes in this patent application.

The description and the drawings of the present document describe examples of embodiment(s) of the present invention and also describe some exemplary optional feature(s) and/or alternative embodiment(s). It will be understood that the embodiments described are for the purpose of illustration and are not intended to limit the invention specifically to those embodiments. Rather, the invention is intended to cover all that is included within the spirit and scope of the invention, including alternatives, variations, modifications, equivalents, and the like.

Figure 2:
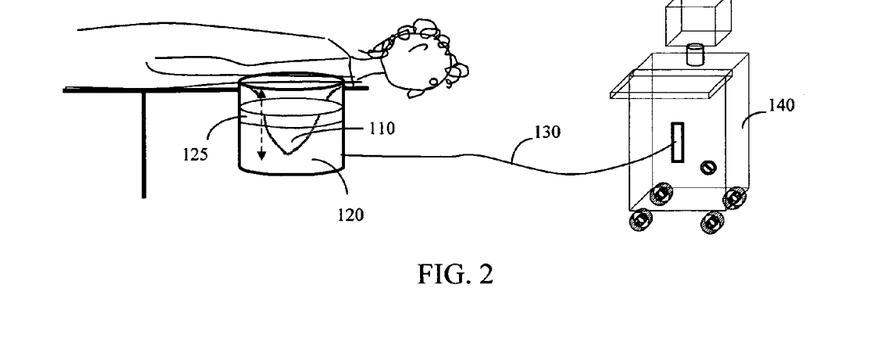
FIG. 2 is a side cross sectional diagram of an ultrasonic scanning system of this invention.

FIG. 2 is a schematic block diagram that shows a three-dimensional (3D) full breast scanning image acquisition system as an embodiment of the present invention. A breast 110 is within or at least substantially within a container 120. The container 120 is filled with liquid, preferably de-bubbled water. An ultrasound probe 125 is disposed in or around the container 120. The ultrasonic probe 125 is preferably an omni-directional high frequency ultrasound probe. In an exemplary embodiment as shown, the ultrasonic probe 125 is controllable to move in the container, for example, along a vertical direction of the container 120 in a linear up and down direction. The image scanning signals when collected by the probe 125 is then transmitted through a cable 130 to an ultrasound system 140 to carry out image display and data collection and analysis functions. As shown in FIG. 2, the ultrasonic probe 125 has a ring shape to move up and down in the container 120 that has a cylindrical shape.

In an alternate embodiment, the interior of the container 120 is lined with a plurality of probe elements. With sufficiently number of probe elements, a physical movement of the probe is not necessary, and it is only necessary to switch on the appropriate probe elements. The omni-directional probe, i.e., transducers, preferably is configured with sufficient probe elements, and/or sufficient mobility of the probe elements that the omni-directional probe can acquire the breast image in 360 degrees.

Figure 3:
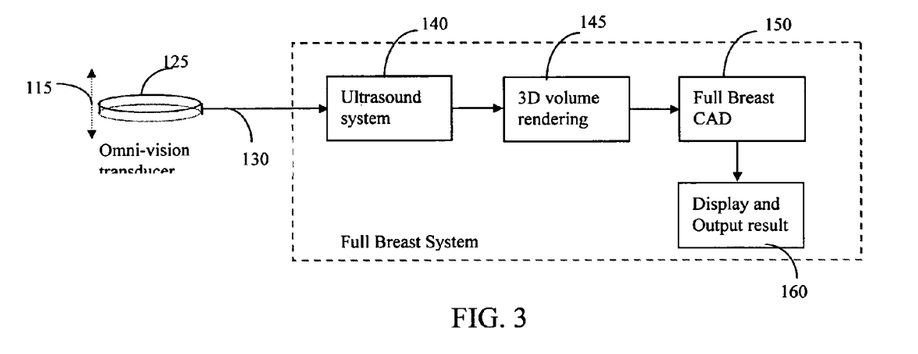
FIG. 3 is a functional block diagram for showing the functions carried out by the ultrasonic image scanning system of FIG. 2.

FIG. 3 shows the movement of the omni-vision transducer as the ultrasonic probe 125 moves along a vertical direction 115. The data of scanning image is transmitted through the cable 130 to the ultrasound system 140. The ultrasound system 140 first carries out a 2D composite image construction, and then the 3D volume rendering process 145 of the three-dimensional image signals followed by performing a full breast CAD process 150 to construct a data array for representing the three dimensional image data. The image scanning results are displayed for diagnosis and as output data for further processes and analyses (160).

In contrast to the conventional freehand and water-bag acoustic scanning approaches, the system as shown above provides an acoustic probe to scan a subject body part from different positions without varying the pressure applied to the subject body part. Furthermore, the probe is now enabled to simultaneously scan the subject body part from non-parallel directions without varying the pressure applied to the subject body part.

The water in the container 120 serves the function as an acoustic coupling between the scanning surface and the breast. The water is preferably de-bubbled water. The water is automatically filled and drained from the container via conduits (not shown). The container is kept hygienic with regular disinfection, and the container may be configured to automatically dispense disinfection agents via a conduit. In one embodiment, the movement of the probe is linear only, without rotation, for the sake of simplicity and reliability. In one embodiment, multiple containers and probes are provided to accommodate different sizes of breasts. Preferably, a wire target of known configuration is provided to the end user to place within the container to provide a test pattern so that the system can calibrate itself for the scan converter algorithm. There is a baffle around each transducer to absorb energy, which may cause acoustic reverberation. The system may be configured to have, for example:

40 mm probe FOV (Field Of View) and 7.5 MHz or higher 128 or 64 elements, 12-20 module per circumference,
20 cm diameter maximum for the acquisition window,
30 cm height, Depending on design choice and depending on application other elements or configuration of similar designs may be also be implemented. The calibration is for the scan converter (R-Theta to Rectangular) algorithm to map all the images from different angles into a circular image. The above numbers represent exemplary implementation of the transducer for each multiplexed module.

Preferably, a scan controller implemented in a computer, e.g., the ultrasound system 140 that includes a scan controller, automatically controls the image scan and data acquisition processes. By properly setting up the control processes, standard types and amount of signals and data are generated and acquired through the image scanning processes. The results of image scanning would then not depend on the level of skill of an image scanner operator and human errors can also be minimized. The speed and cost of carrying out such scanning process is also significantly reduced while more reliable and accurate diagnosis can be provided by consistently using standardized scanning configurations and data analysis processes carried out by highly accurate CAD and image processing systems for detail review by radiologist. The 3D volume image provides a consistent basis for correlation and comparison over a duration of time to track whether there are changes in the scanned image over time.

Referring to FIGS. 2 and 3 again, the ultrasound system 140 may be implemented as a sonogram system that includes a computer-controlled acoustic probe 125. The acoustic probe 125 scans the subject body part from different positions without varying the pressure applied to the subject body part and preferably from different non-parallel directions without physically touching the subject body part. The de-bubbled water serves the function as coupling medium for transmitting acoustic waves for receiving a scanning image signals back from the subject body part. The scanning image signals are then received and stored based on the positions of the probes and the timing sequence of these signals for rendering a volumetric configuration for the scanned body part by applying appropriate tomography techniques.

For actual implementations, the ultrasonic probes may utilize probe technology with fine AWG cable. An HV 20220 or Hitachi 3290 chip or the like may be used. A card-bus connector (68 pin) or the like may be used. Reverb cancellation is preferably included according to any competent technique, for example, any competent conventional reverb cancellation technique. The card-bus connector provides the multi-wire connection in between the probe module. After many single angle probe modules are linked together, it forms a complete 2D circulator probe. The final outputs are brought to the ultrasound system 140 through fine gauge wire cable (e.g. AWG 36). The HV20220 is a high voltage semiconductor multiplex switch. It is used in the single probe module to provide the real time signal routing. When the acoustic wave travels in the water, it may bounce back and forth in the media. The baffle serves the purpose of muting this secondary reflection artifact. The controller may also include a CAD capability for processing three-dimensional data to obtain accurate compound tomographic image.

Figure 4:
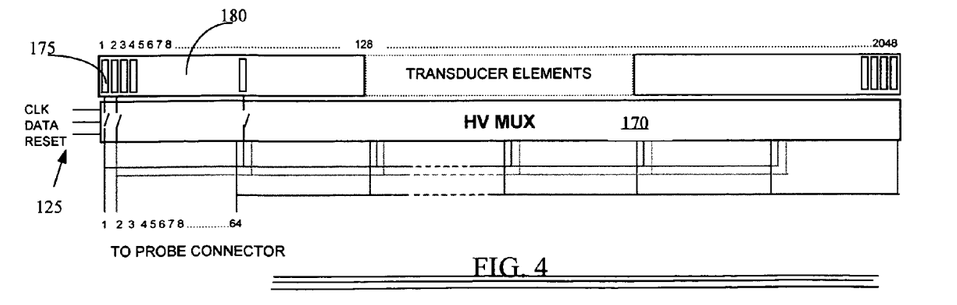
FIG. 4 is a linear diagram for showing arrangement of MLA elements to channel bus connections.
Figure 5:
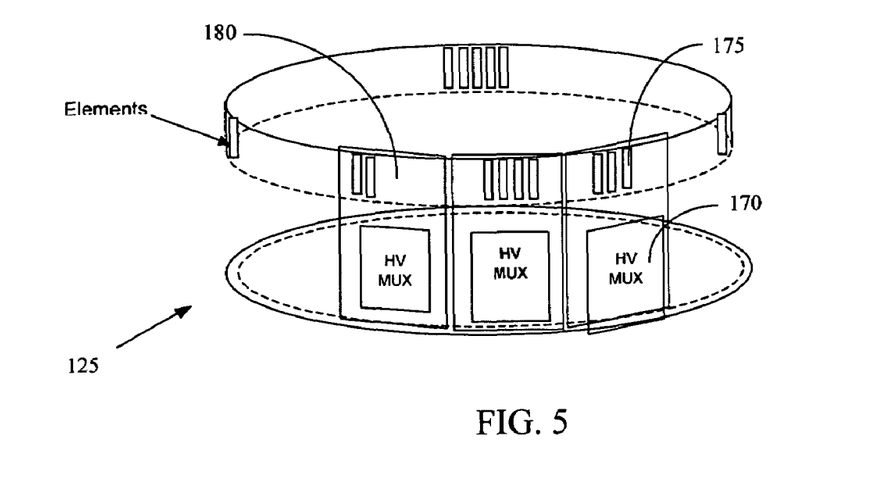
FIG. 5 is a linear diagram for showing arrangement of MLA (Multiplexed Linear Array) elements to channel bus connections.

Referring to FIG. 4 for the configuration of the ultrasonic probes implemented with omni-vision transducer arranged according to the MLA configuration to multiplex the element (>2048) bus to the channel (64) bus. Omni-vision allows the image to be acquired at 360 degree in real time. The MLA provides the signal routing from each individual transducer module to the ultrasound system. In a specific embodiment, there are 2048 elements arranged in a circle, and the HV multiplexer 170 is configured in a way that the output from every sixty-four transducer elements 175 are multiplexed together. In each individual probe module, there is an array of transducers with High Voltage Multiplexer. The array further consists of 64-128 elements of piezo-transducer in one substrate in order to form a focus beam electronically. Each MUX 170 has a separate control bit to turn the HV switch on/off. In the beginning after the system reset all these HV switches, logic high will be shifted into the HV MUX control register to connect the selected element to the output until all 64 elements are turned on, thereafter, it will slide the element until it reaches the end of the first group of 128 elements. Then the transducer element 175 switches to the next group and repeat the same procedures. Referring to FIG. 5, each group of transducers supported on a printed circuit board module 180 has a width of 40 mm. The circumference is sixty-four centimeters, i.e., about twenty centimeter diameters, to accommodate sixteen transducer groups supported on the PCB 180. Each printed circuit board (PCB) module 180 has one hundred and twenty-eight (128) element transducers 175 and HV multiplexer 170. Inter-module connection can be a flex cable with miniature high-density (>68) card bus connector, or a circular PCB at the bottom, or even a direct connection in between PCB. The Ultrasound system will treat the omni-vision circular probe as a circular MLA with 2048 elements in sixteen (16) groups.

Instead of the MLA configuration as described above, an alternate embodiment is to place the 2048 probe elements in a uniform circular arrangement, instead of 16 modules at 16 different angles, for acquiring each image vector in a constant arc distance and reconstruct the image. Additional efforts would be required to build and align these individually placed probe elements. The acoustic energy probably would be concentrated around the center location and may cause the energy intensity to exceed the governmental regulatory limits, e.g., FDA limit. The image density vectors may not uniformly distributed with higher density distributed in the center and much lower density distribute on the edges and that may affect the image quality due to these non-uniform distributions of image density vectors. A further limitation for such configuration is that it cannot compound the image with different speckle distribution since the speckle changes when the image vector is acquired from different angle. However, since this embodiment has the advantage that the configuration appears simple and easy to implement conceptually, it is also included as one of exemplary embodiments in this invention as well. Further investigations and analyses and future technological developments may prove this configuration to be a preferred implementation for particular applications.

Another configuration for implementing this invention is to apply one module, or several modules as ultrasonic probes for transmitting ultrasound waves to the scanned body object for receiving the feedback signals to construct a probing image. The motor is applied to drive the probing module or modules to circularly move around the container to acquire the image by collecting data from an image scan with the ultrasound probes placed around three hundred and sixty degrees. Such operation may require longer period of time than the distributed scanning probe configuration as described above. Another concern of high-speed motion of the ultrasound probes in the container is the generation of bubbles that may affect the accuracy of the image scanning. The circular move around the peripheral edge of the container also leads to more complicate cable arrangements. Furthermore, alignment and angular calibration operations of the scanning probes may be necessary when multiple shots in different angles are likely to produce overlapping and compound images.

Figure 6:
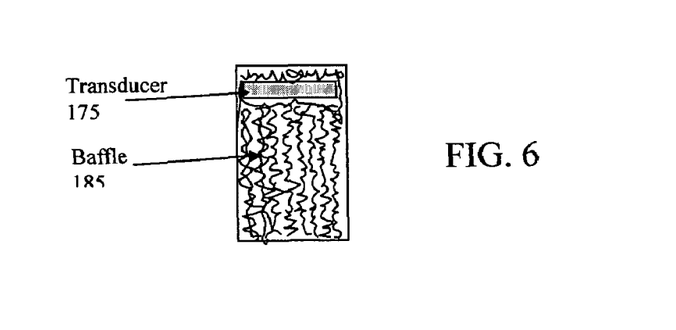
FIG. 6 is a top view of a module covered with baffle.

FIG. 6 shows the areas 185 on a PCB other than the transducer 175. For the purpose of absorbing the acoustic energy to prevent reverb echo, the areas between the transducers are covered with rubber baffle formed with an irregular shape.

Figure 7:
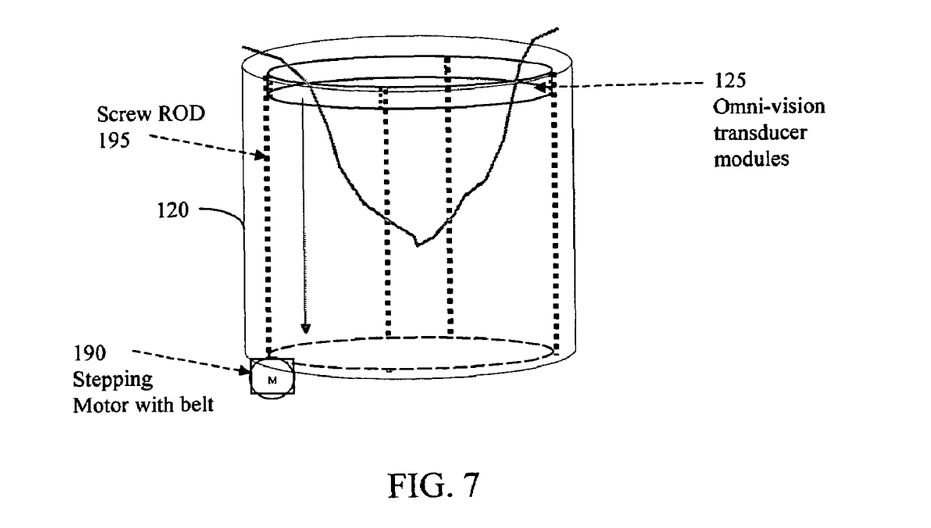
FIG. 7 is a side cross sectional view of container implemented with a stepping motor for vertically moving a scanning sensor along screw rods.

FIG. 7 illustrates that the whole transducer 125 can be moved up and down with a stepping motor 190 supporting the movements with screw rods 195. There is preferably no rotation involved. The movements of the transducer 125 can be controlled by a controller included in the ultrasound system 140 implemented with a software that sets a maximum displacement. The maximum displacement may also be based on the length of the subject body image for scanning. When there is no echo according to the reflected signals from the whole image, it is determined that the probe 125 has moved to the end of the tissue volume 110. The control of the stage motor 190 is through the RS232 or USB port or other similar or equivalent connecting ports from a host personal computer that may be implemented in the ultrasound system 140.

Figure 8:
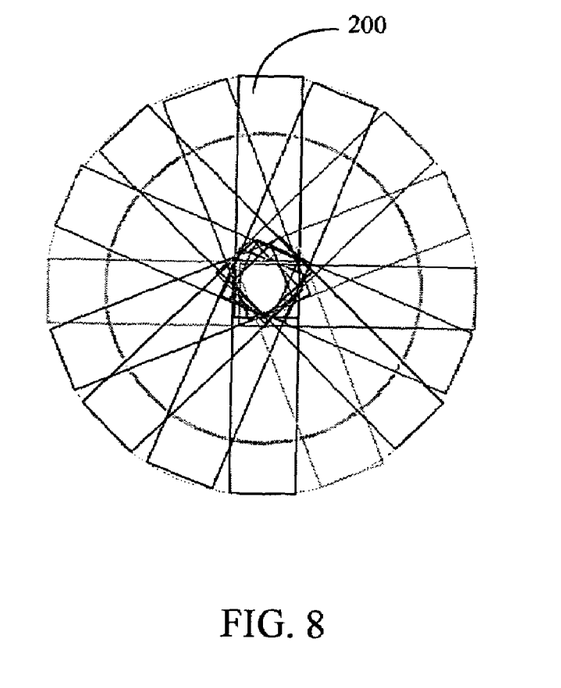
FIG. 8 is a top view of slices for showing a composite image of data acquisition during the scan process.
Figure 9:
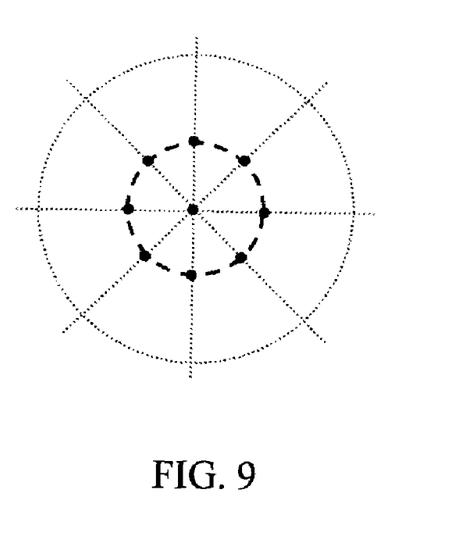
FIG. 9 illustrates a calibration pattern.

Referring to FIG. 8 for the divisions as slices 200 of the image data acquired from the transducers distributed over a circumference covering multiple rectangular areas wherein each set of transducers are receiving signals from a different angle. With the acquisition of the same image area from different angles, a composite image is formed as the tomography using image processing techniques similar to MRI image processing. With the motor movement, a volume image can be acquired for the 3D viewing. For a 20 cm diameter image slice, each segment image only needs to process of a length of 10 cm. An array probe can be utilized that is competent for such penetration; for example, a 7.5 MHz linear array transducer module may be used. For the image acquired from each module, the system may perform a scan conversion with different angles and compound the images together. Referring to FIG. 9, for the purpose of assuring the images are aligned properly, there is a wire pattern phantom used to calibrate during the image installation. A phantom is any dummy target to simulate the echo reflected from scanned object according to transmission of ultrasound waves. The wire targets are in a fixture for calibration as described above. The purpose of such calibration is mainly for adjusting the geometric error due to the assembly of the 16 probe modules when operated together during the process of a scan conversion.

A CAD system and methods are incorporated that characterize the features of the disease and make a best estimation to guide the radiologist in the radiologist's review. A 3D volume rendering display can be shown on the screen to help the doctor make the doctor's review. The CAD usually starts from volume rendering the 3D data sets of image, and display the 3D image on the screen. The user can rotate the image in any angle, set the different opacities of the object to identify the suspicious lesion. An advanced CAD algorithm can analyze the image with the cancer features, for instance, the smoothness of the lesion boarder, the shadow behind the lesion, etc. Such kind of information can help, not to replace, the radiologist in making the decision. The surgeon can also have an idea on the 3D tumor before the operation, and the oncologist can trace the tumor size during the treatment.

Figure 10:
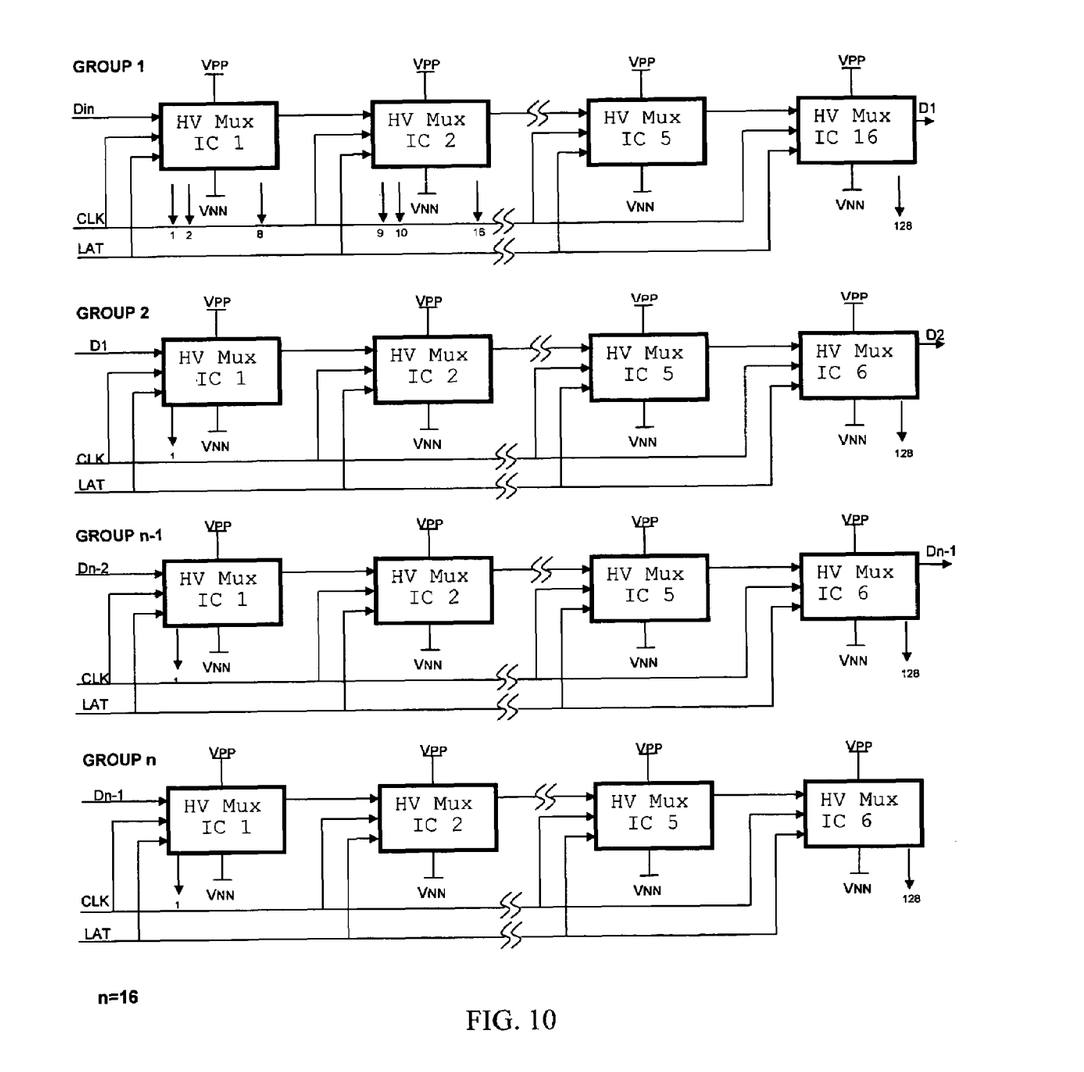
FIG. 10 is a connection diagram for transducers connected to multiplexed for transmitting multiplexed scanning measurement signals to signal processing controller.

Referring to FIG. 10 for an implementation of the omni-directional probe HV MUX connection. There are 2048 transducer elements of Omni-vision probe multiplexed in such a way that 64 (or less) consecutive elements are allowed for selection at any one time. Each time an aperture of image scanning is decided, control data are clocked into the shift register of the HV Mux Ics (Hitachi HVmux3290), after transferring 64 bits '1', the system will start to clock in '0' for each line increment until it reaches to the end of the group, and the setting moves to the next group. At the output of the HV Mux, module 1 to 16, element number 1 and 65 are connected together and become CH0, that is equal to element 1. Likewise, module 1 to 16, element number 2 and 66 are connected together and become CH1 and so forth.

Figure 11:
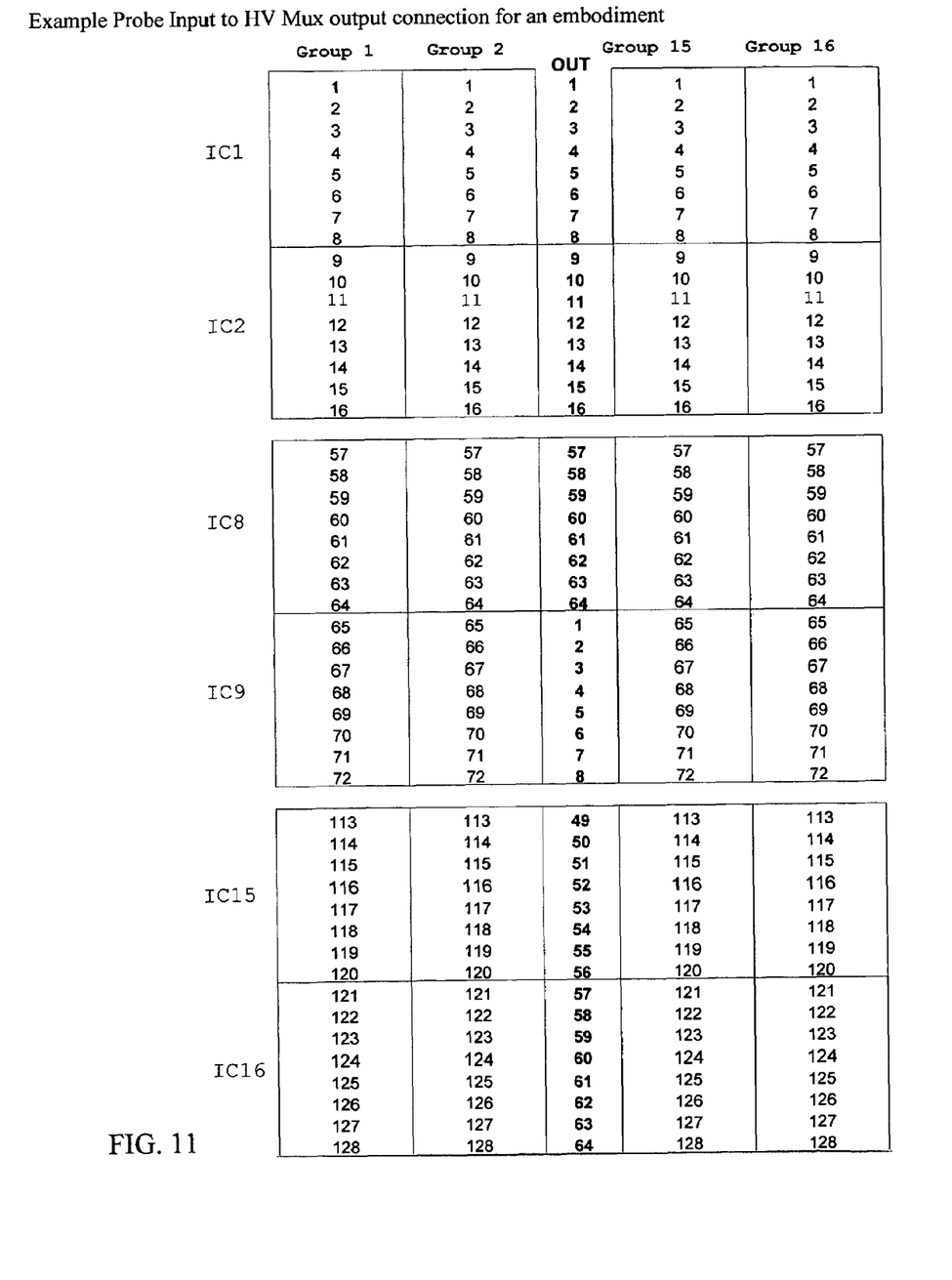
FIG. 11 is a table for showing an example of probe input to HV Mux output connection implemented in a specific embodiment.

An example Probe Input to HV Mux output connection for an embodiment is shown in FIG. 11. The arrangement of this connection allows the invented probe device to be compatible with the conventional ultrasound system therefore, the scan conversion algorithm and the hardware platform can be adapted for this purpose.

Again, it is to be understood that the embodiments described are for the purpose of illustration and are not intended to limit the invention specifically to those embodiments. For example, although the subject body part (e.g., breast) is shown as being immersed into an open container from the top, the container can also be placed onto a subject body part from any other direction. For example, the container can be placed onto a subject body part, and the container can have a conformal lip that conforms to the body part, and a seal can be made against the body part using any competent sealant, and then the container may be filled. Or, the container may be closed on its one otherwise-open end by a thin, flexible membrane, and the membrane can make contact with, and conform to the contours of, the subject body part, perhaps aided by an acoustic couplant to assure good acoustic coupling. Still other variations are within the scope of the present invention.

I claim:

1. An ultrasonic image scanning system for scanning an organic object comprising:
   a plurality of modules, each module comprising a high voltage multiplexer and a plurality of ultrasonic transducers,
   a container for containing a coupling medium surrounded by each of the high voltage multiplexers and the plurality of ultrasonic transducers, each module disposed immediately adjacent to said container for transmitting an ultrasonic signal to said organic object immersing directly in said coupling medium, whereby a simultaneous multiple direction scanning process may be carried out without physically contacting said organic object; and said plurality of ultrasonic transducers further receiving echo signals from said organic object transmitted in said coupling medium wherein said ultrasonic signal transmitted to and said echo signal transmitted from said organic object are transmitted completely through and within said coupling medium for improving an accuracy of an ultrasonic image scan; and
   a baffle layer positioned in the module in the areas between each of the plurality of ultrasonic transducers to reduce an acoustic reverberation associated with the scanning.

2. The ultrasonic image scanning system of claim 1 wherein:
   said ultrasound transducers are arranged on a same horizontal level surrounding said container for simplifying an image geometrical and signal transmission and echoing analysis based on a configuration of the same horizontal level.

3. The ultrasonic image scanning system of claim 1 wherein:
   said ultrasound transducers are distributed and substantially surrounding an entire perimeter of said container.

4. The ultrasonic image scanning system of claim 1 wherein:

said ultrasound transducers are distributed substantially at symmetrical angular positions at approximately equal divisions of 360 degrees over an entire perimeter of said container.

5. The ultrasonic image scanning system of claim 1 wherein:
said ultrasound transducers are distributed substantially around an entire perimeter of said container wherein said transducers are further movable over a direction perpendicular to a 2D scan plane of said transducers along sidewalls of said container for a real time three dimensional (3D) image data acquisition.

6. The ultrasonic image scanning system of claim 1 wherein:
the baffle layer has an irregular shape.

7. The ultrasonic image scanning system of claim 1 wherein the high voltage (HV) semiconductor multiplexer integrated circuit (IC) is connected to an array of ultrasound probes for real time scanning and data acquisition.

8. The ultrasonic image scanning system of claim 1 wherein:
said coupling medium further comprises de-bubbled fluid.

9. The ultrasonic image scanning system of claim 1 further comprising:
a wire phantom for carrying out a scan conversion geometric calibration.

10. The ultrasonic image scanning system of claim 1 further comprising:
an image data processor for performing a three-dimensional volume and/or surface rendering for representing a scanned image of said organic object.

11. The ultrasonic image scanning system of claim 1 further comprising:
a computer aided diagnostic (CAD) system for processing a set of image scan data for constructing and presenting tissue structural characteristics details of said organic object according to said set of image scan data.

12. The ultrasonic image scanning system of claim 1 further comprising:
a dense breast screen device to prescreen a dense breast as an organic object for carrying out an image scan by said ultrasonic image scanning system.

13. The ultrasonic image scanning system of claim 1 wherein:
said ultrasound transducers are distributed substantially with a uniform circular arrangement for acquiring an ultrasonic image vector in a constant arc distance for reconstructing an image of the organic object.

14. The ultrasonic image scanning system of claim 1 wherein:
said ultrasound transducers further comprising omni-directional high frequency ultrasound probes.

15. The ultrasonic image scanning system of claim 1 wherein:
said ultrasound transducers are further distributed over an entire interior surface of said container with a sufficient number of ultrasound transducers to capture a three-dimensional image of said organic object without requiring a movement of said ultrasound transducers.

16. The ultrasonic image scanning system of claim 1 further comprising:
a scan controller to automatically control an image scanning process and data acquisition by controlling said ultrasound transducers with a standard scanning procedure.

17. The ultrasonic image scanning system of claim 16 further comprising:
a card bus connector to transmit signals between said scan controller and said ultrasound transducers.

18. The ultrasonic image scanning system of claim 17 further comprising:
said card bus connector further comprising a high voltage semiconductor multiplex switch for controlling a real time signal routing.

19. The ultrasonic image scanning system of claim 1 wherein:
said ultrasound transducers are controllable to move around to different angular positions of said container for transmitting said ultrasonic signal to said organic object through said coupling medium without deforming said organic object.

20. A method for ultrasonically scanning an organic object comprising:
filling a container with a coupling medium
placing a plurality of modules comprising a plurality of ultrasonic transducers immediately around said container for transmitting an ultrasonic signal to and receiving echo signals from said organic object, each module further comprising a high voltage multiplexer;
immersing directly in said coupling medium for carrying out a simultaneous multiple direction scanning process without physically contacting said organic object wherein said ultrasonic signals transmitted to and said echo signals transmitted from said organic object are transmitted completely through and within said coupling medium for improving an accuracy of an ultrasonic image scanning; and
providing a baffle layer within the module in the areas between each of the plurality of ultrasonic transducers to reduce an acoustic reverberation using the baffle layer.

21. The method of claim 20 further comprising:
arranging said plurality of ultrasound transducers on a same horizontal level surrounding said container for simplifying an image geometrical and signal transmission and echoing analysis based on a configuration of the same horizontal level.

22. The method of claim 20 further comprising:
distributing said plurality of ultrasound transducers to substantially surround an entire perimeter of said container.

23. The method of claim 20 further comprising:
distributing a plurality of ultrasound transducers substantially at symmetrical angular positions at approximately equal divisions of 360 degrees over an entire perimeter of said container.

24. The method of claim 20 further comprising:
distributing a plurality of ultrasound transducers substantially around an entire perimeter of said container wherein said transducers are further movable over a direction perpendicular to a 2D scan plane of said transducers along sidewalls of said container for a real time three dimensional (3D) image data acquisition.

25. The method of claim 20 further comprising:
distributing said plurality of ultrasonic transducers over an entire interior surface of said container with sufficient number of ultrasonic transducers to capture a three-dimensional image of said organic object without requiring a movement of said ultrasonic transducers.

26. An ultrasonic image scanning system for scanning an organic object comprising:
a container for containing a coupling medium for transmitting an ultrasonic signal to said organic object disposed therein, whereby a simultaneous multiple direction scanning process may be carried out without physically contacting said organic object, and the container comprising sidewalls;

a plurality of modules, each module comprising a high voltage multiplexer and a plurality of ultrasonic transducers, the plurality of ultrasound transducers for transmitting said ultrasonic signal to said organic object through said coupling medium without asserting an image deforming pressure to said organic object, the modules distributed substantially around a two-dimensional perimeter of said container, the ultrasound transducers distributed substantially at symmetrical angular positions at approximately equal divisions of 360 degrees over the two-dimensional perimeter of said container, the transducers further movable over a vertical direction along sidewalls of said container for a real time three dimensional image data acquisition; and a baffle layer. positioned in the areas between each of the plurality of ultrasonic transducers to reduce an acoustic reverberation associated with the scanning the organic object.

27. The system of claim 26 wherein the baffle layer comprises rubber and the module comprises a printed circuit board that supports each of the ultrasonic transducers and the high voltage multiplexer.

28. The system of claim 26 wherein the baffle layer is formed with an irregular shape.

* * * * *